United States Patent [19]
Latorre

[11] 4,127,118
[45] Nov. 28, 1978

[54] METHOD OF EFFECTING AND ENHANCING AN ERECTION

[76] Inventor: Alvaro Latorre, 721 Cervantes, El Paso, Tex. 79922

[21] Appl. No.: 778,047

[22] Filed: Mar. 16, 1977

[51] Int. Cl.² .............................................. A61F 5/00
[52] U.S. Cl. .................................. 128/79; 128/214.2
[58] Field of Search ................... 128/79, 214.2, 214 R, 128/215

[56] References Cited
U.S. PATENT DOCUMENTS

| | | | |
|---|---|---|---|
| 3,552,394 | 1/1971 | Horn | 128/214.2 |
| 4,009,711 | 3/1977 | Uson | 128/79 |

*Primary Examiner*—Lawrence W. Trapp
*Attorney, Agent, or Firm*—Bruce Newell

[57] ABSTRACT

A method of alleviating and treating male impotence by effecting and enhancing an erection by injecting into the penis an appropriate vasodilator, a sympathomimetic amine, or an adrenergic blocking agent.

11 Claims, 7 Drawing Figures

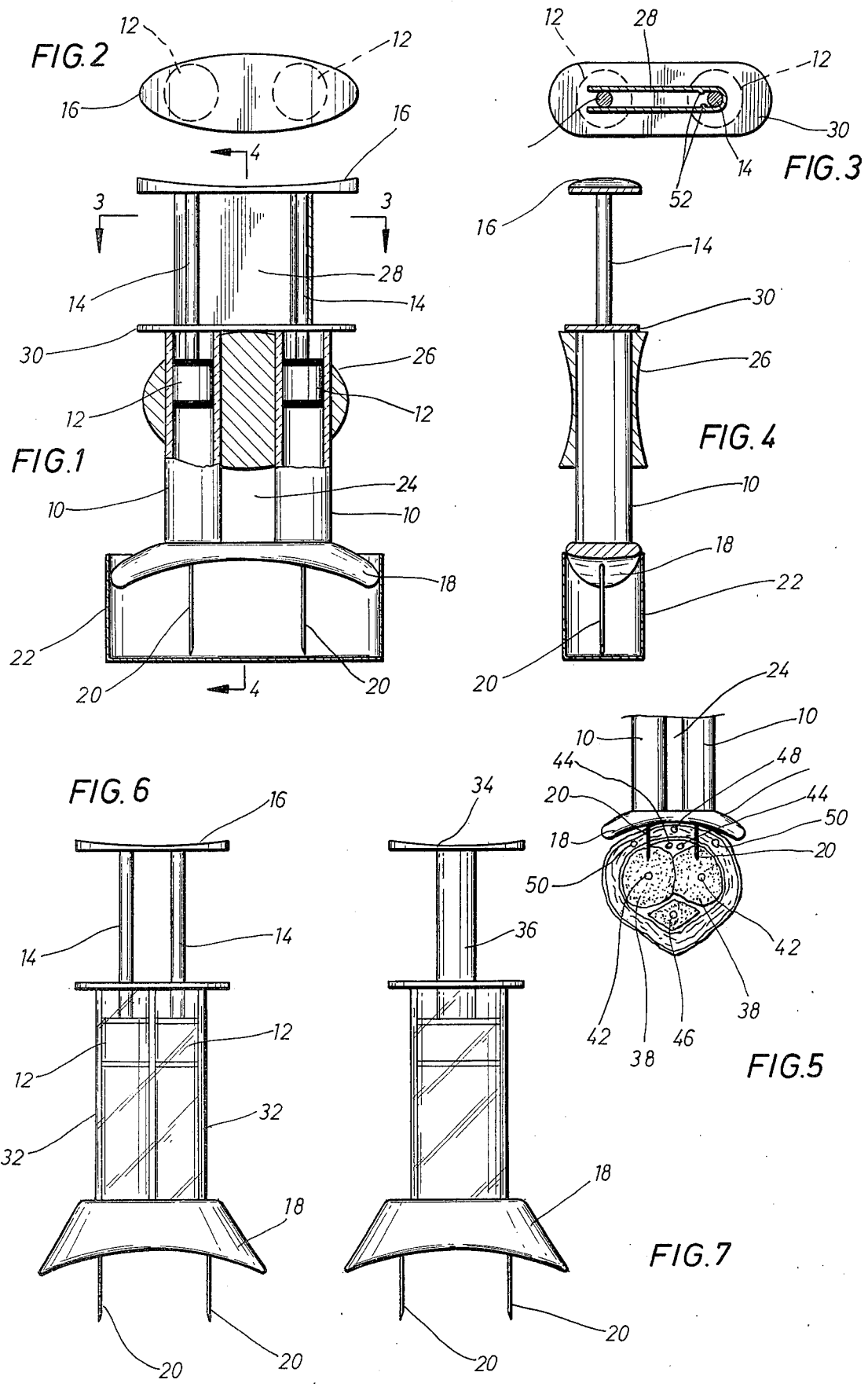

METHOD OF EFFECTING AND ENHANCING AN ERECTION

BACKGROUND OF THE INVENTION

This invention relates to the problem of male impotence and is a method of temporarily alleviating and treating impotence by aiding in producing, enhancing, and sustaining an erection of the penis.

The ability to attain and maintain an adequate erection has long been a problem to older men as well as to some younger men experiencing psychogenic or physiologic impotence due to various factors. This invention is the first really viable solution to this problem, and is a solution involving no tourniquets, straps, bands, sleeves, or other supportive devices used in the past to aid in effecting an erection. There have been numerous attempts to treat impotence by the administration of certain drugs, but none thus far has been really successful in aiding the impotent.

Whether the impotence is absolute (involving all sexual modalities), total (also affecting all sexual functions, though not necessarily libido), or partial (affecting the rigidity or duration of erection), or whether the cause of impotence is organic (due to structural changes, disease, or some demonstrable functional impairment anywhere in the sexual system), psychogenic (due to psychological factors such as depression or aversion to a particular sex partner), or physiologic (due to old age or sexual satiation), the result is the same: inability to engage in sexual activity due (at least partially) to the lack of an adequate erection. Impotence may be defined more fully, however, as the inability to develop or sustain an erection of the penis sufficient to conclude coitus or orgasm and ejaculation to the male's own satisfaction. Impotence treatment methods are generally, however, concerned with the erection aspect and not ejaculatory impotence, which is relatively rare.

The penis becomes erect when certain tissues (e.g., the corpora cavernosa, 38 in FIG. 5) in the central portion of the penis become widely dilated with blood, thereby causing them to become less flaccid, and in turn causing an erection.

While the vast majority of impotence treatment methods have been concerned with exogenous nervous stimulation of the organ to produce an erection by, for example, local stimulation via vibration, many blood constrictive devices have been proposed throughout this century for producing and enhancing an erection. Typically, these are adjustable, tourniquet-like rubber band devices which are designed to fit tightly around the shaft of the penis and thereby restrict the flow of blood from the penis through the surface veins, as well as the deeper dorsal vein, to prolong an erection. For example, Atchley U.S. Pat. No. 3,636,948 discloses an adjustable device designed to fit the contour of the penis, to exert greater pressure on the area where the subcutaneous (surface) veins are located, thereby restricting the blood exiting the penis through the peripheral veins. Similarly, Miller U.S. Pat. No. 2,818,855 is ineffective for depressing the deep dorsal vein and preventing or significantly restricting flow of blood there. There have been numerous other attempts to solve the problem, but all exhibit various disadvantages to the user, and sometimes to the female sex partner, such as extreme discomfort during intercourse, to the extent that users might not achieve the desired usefulness as frequently as desired and to the extent preferred. All the external devices previously proposed have the psychological disadvantage of being an impediment to the sex act, and the operational disadvantage that their duration of effectiveness is relatively short.

Impotence associated with androgen deficiency has long been thought by certain medical factions to be treatable by the administration of sex hormones via synthetic preparations such as methyl testosterone and various esters, including propionate, deconate, and enanthate, as well as a number of testosterone-aphrodisiac combinations. Androgen levels in the blood are known to decrease gradually with age, but the extent to which reduced hormone output seriously interferes with the sexual function is not really known, and there is some controversy as to whether the level of testosterone in blood plasma of impotent men is a significant indicator of its value in treatment. The prevailing view is that there is a definite correlation between testosterone levels and impotence. But see Racey, et al., *Testosterone in Impotent Men*, 59 Journal of Endocrinology xxiii (Nov. 1973), wherein it is reported that the concentration of testosterone in blood plasma of impotent patients did not differ significantly from that of a laboratory control group.

In some cases, however, steroid replacement therapy (periodic administration of androgens) has been found to reactivate lagging sexual response. Testosterone deficiency can cause sudden marked reduction in ejaculatory pressure and seminal fluid output, and repeated prostatic pain from sustained contraction of the organ during intercourse. Accordingly, extended experimental studies of testosterone therapy have been conducted, some with good results.

Mesterolone is a synthesized androgen which is distinguished from most other orally effective steroids by the lack of a 17-alkyl group. The compound has an androgenic effect equal to that of methyl testosterone, but is superior in effect in that it has virtually no toxicity to humans if administered within conventional therapeutic dose ranges. Also, unlike methyl testosterone, it has not been found to inhibit endogenous testosterone formation or spermatogenesis. Mesterolone has, however, been found to be a poor means of treating impotence. See Cooper and Ismail, *A Pilot Study of Mesterolone and Impotence*, 26 Psychopharmacologia 379, 380 (1972). The lack of response to mesterolone indicates that testosterone levels per se may be irrelevant to adult potency, and thus lends credence to the proposition that the administration of testosterone and other synthesized androgens are not only ineffective in the long run, but possibly harmful as well.

Despite claims by some doctors such as Cooper and Ismail, of therapeutic success from testosterone treatments, the administration of exogenous hormones has several pharmacologic disadvantages. For example, methyl testosterone must be taken subcutaneously or bucally and is felt by some researchers to cause severe toxic effects such as cholestatic jaundice. Parenterally administered testosterone esters, while less toxic and more certainly absorbed than methyl testosterone, have all the drawbacks of intramuscular administration; not only is there more pain, but the deeply injected medication frequently isn't absorbed adequately, and the risk of deeper and more widespread infection is more serious. Also, long-term administration of these synthetic compounds may inhibit endogenous testosterone formation and spermatogenesis by supressing pituitary gonadotrophins, thereby resulting in glandular tisuse atrophy because of disuse.

The risk of atrophy is heightened by certain studies which indicate that when testosterone is administered for the treatment of impotence associated with androgen deficiency, an adequate clinical response may require the maintenance of serum testosterone concentrations at a higher-than-normal level, higher than the conventional therapeutic dosage of 500 milligrams intramuscularly per week. See Sternberg, *Testosterone in High Dosage for the Treatment of Impotence: Effect on Serum FSH When Combined With Chorionic Gonadotropin*, 21 Journal of the American Geriatrics Society 271, 272 (1973). More conclusive studies involving treatment with testosterone are needed, as some researchers are extremely concerned that, in addition to testosterone's problems of ineffectiveness and gland atrophy, its use enhances existing cancers of the prostate gland.

Because of the uncertainty and the problems involved in the administration of testosterone in the treatment of impotence, there have been numerous non-androgen related attempts to treat the impotence problem, including treatments with yohimbine (an alkaloid from the bark of the yohimbihi tree), damiana, ginseng, levodopa (L-dihydrophenylalanine, metabolic precursor of the brain neurotransmitter amines — dopamine and norepinephrine), hydergine (a combination of three hydrogenated ergot alkaloids — adrenergic blocking agents), clomiphene (formerly used only as an ovulatory stimulant), phosphorous, strychnine, and cantharides (Spanish Fly). These are generally administered orally with varying degrees of success, some with significant side effects.

One androgen compound is a drug comprised of equal amounts of nux vomica extract, methyl testosterone, and yohimbine, marketed by Bentex Pharmaceutical Company of Houston under the mark Afrodex, found in clinical studies to provide a significant treatment effect in the treatment of male impotence. See Roberts and Sloboda, *Afrodex vs. Plecebo in the Treatment of Male Impotence: Statistical Analysis of Two Double-Blind Crossover Studies*, 16 Current Therapeutic Research 96 (1974). Afrodex, previously prescribed in 15 milligram oral dosages, three times a day, is no longer available on the market because its effectiveness was questionable.

Another non-steroid drug which has been found to have a significant effect in raising the level of urinary steroid matabolites, including testosterone in both normal and corticosteriod deficient males, is clomiphene, a non-steroid triethylene derivative. Only limited pilot studies have been conducted to determine its value as a possible alternative drug treatment in impotence. See Cooper, et al, *The Effects of Clomiphene in Impotence: A clinical and Endocrine Study*, 120 British Journal of Psychiatry 327 (1972).

The various problems involved in androgen treatments make it apparent that non-steroid treatment of impotence is the logical answer. The problem is to find a drug that will work in treating impotence, and to devise a means of administration that is both effective and harmless over a long period of time. Because of the unreliability and potential side effects involved in the oral administration of certain drugs that may be useful in treating impotence, the answer is a way to treat the impotence directly by effecting an erection. This is best done by administration into the penis itself, because the dosage may then be minimized since virtually all the dose acts directly on the penile tissues.

The subject invention provides a way to produce and enhance and even maintain an erection without the attendant difficulties inherent in oral administration of drugs or in use of a device or appliance that must be worn during intercourse. Various creams and rubbing compounds are available for external treatment of the skin surface of the penis, but nothing for treating the tissues which actually provide the erection. The invention, involving nothing which may be annoying or even apparent to the female sex partner, provides such a way by means of the injection of certain drugs into the corpora cavernosa of the penis with a hypodermic syringe.

Preferably, a dual needle syringe is used to inject both corpora cavernosa at the same time, because it's desirable to make injections simultaneously in cases where multiple injections are to be made relatively close together, as the patient will experience only one sensation of pain if the distance between the two needles does not exceed the distance at which the surface pain sensors of the skin can distinguish between single and multiple locations of pain. The two-point sensation of pain distance varies over different parts of the body.

The basic concept of the dual needle syringe is old, and numerous patents have been granted on various devices, for example Horn U.S. Pat. No. 3,552,394, which discloses a dual hypodermic syringe with integrally molded barrels and independent plungers and needles, apparently of the conventional variety. Accordingly, the subject invention provides a new way to produce an erection by simultaneously injecting an appropriate drug into the corpora cavernosa of the penis with a novel syringe designed expressly for this purpose.

SUMMARY OF THE INVENTION

The invention is a method of treating impotence by effecting and enhancing an erection by injecting a vasodialator directly into the penis.

DESCRIPTION OF THE DRAWINGS

FIG. 1 shows an overall view (partially cutaway) of the syringe used in connection with the invention, and clearly illustrates the dual needle arrangement with the two barrels 10 connected by the integrally molded housing 24 forming the barrel grip 26, the barrels 10, and the curved end member 18, which abuts the penis when the needles 20 are fully inserted, as in FIG. 5. The plungers 12 are depressed by the plunger rods 14 and in turn, by the single depressor 16. A protective cap 22 is shown on the syringe in FIGS. 1 and 4. All illustrations are greatly enlarged to clarify details of the syringe.

FIG. 2 is a top view of the depressor 16 shown in FIG. 1, and illustrates the shape of the depressor and its location with respect to the plungers 12 (shown in dotted lines) below it.

FIG. 3 is a cross section of the syringe shown in FIG. 1, and in the direction and at the location indicated in FIG. 1, viewed toward the syringe's top member 30. FIG. 3 illustrates the configuration of the plungers 12 (shown in dotted lines) and the plunger rods 14 and shows the protective clip 28 attached onto the plunger rods 14 to prevent inadvertent closure of the plungers 12 before the syringe is used.

FIG. 4 is a cross section of the syringe shown in FIG. 1, in the direction and at the location indicated in FIG. 1, and illustrates the elevational details of the syringe, especially the barrel grip 26, the depressor 16, and the curved end member 18.

FIG. 5 illustrates the syringe in use, the needles shown injected into the penis, shown here in cross section.

FIGS. 6 and 7 illustrate different embodiments of the dual needle syringe, FIG. 6 being a closer barrel configuration, requiring passageways from the closer barrels 32 to the more distant, but still parallel, needles 20, and FIG. 7 a single barrel version having both needles 20 connected to the lower end of the barrel 33.

DESCRIPTION OF THE INVENTION

The invention is a method of treating impotence by effecting and enhancing an erection of the penis without physiologic nervous stimulation. Preferably, the method is injection into the corpora cavernosa of the penis a predetermined amount of an appropriate vasodilator, including a sympathomimetic amine or an adrenergic blocking agent. Other agents within the histamine and epinephrine groups may also be used when considered appropriate. The drugs used in connection with the subject invention are all nonsteriod drugs, a very important consideration since continued treatment with steroids may result in atrophy of the user's hormone producing glands, or may enhance growth of cancerous tissues.

These drugs, discussed in detail below, are preferably injected simultaneously into each of the corpora cavernosa with a special, dual needle syringe, as shown in FIG. 5, illustrating the needles 20 injected into the corpora cavernosa tissues 38 from the dorsal side of the penis. The erectile tissue of the penis, the corpus cavernosum 38 and the corpus spongiosum 40, is composed of large venous sinuses which contain relatively little blood when the penis is flaccid, but which become very dilated when blood is trapped in them. The dilation of this tissue material with blood is thus the desired objective, with the further objective of effecting and maintaining a hard erection of the organ.

Normally, an erection has two steps: first some nervous stimulation, and then vasodilation of the arteries through which blood flows in the penis. The stimulation of the nervous fibers in the penis may emanate from the central nervous system or from local stimulation of the organ. The nervous stimulation induces vasodilation of the profunda arteries 42 and the dorsal arteries 44 (FIG. 5), through which the primary erectile tissues of the penis, the corpora cavernosa 38, receive blood and gradually become engorged and, in turn, less flaccid. The corpus spongiosum 40, which surrounds the urethra 46 and is separated vascularly from the corpora cavernosa 38, also becomes engorged with blood and thus contributes to the expansion and rigidity of the organ, but its much smaller size, relative to the corpora cavernosa, renders its importance much less critical.

If the arteries are not adequately vasodilated, and if the erectile tissues and muscular structure of the penis do not adequately constrict blood flow from the corpora cavernosa and the corpora spongiosa through the deep dorsal vein 43, the subcutaneous dorsal vein 48, and the subcutaneous lateral veins 50, then some means of doing these things is necessary to effect an erection or to enhance an unsatisfactory erection. Injection of an appropriate vasodilator into the corpora cavernosa will dilate the profunda and dorsal arteries, thereby allowing much blood to come into the corpora cavernosa, engorging them into a much larger volume and significantly constricting the aforementioned veins, thereby reducing the blood flow from the penis. The result is vasodilation without physiologic nervous stimulation. The subject invention thus allows blood to flow freely into the penis in the normal circulatory process, but restricts blood from leaving the organ, thereby resulting in dilation of the corpora cavernosa, partial constriction of the exiting veins, and thus an erection.

While any vasodilator that adequately opens the blood vessels will suffice for the subject invention's treatment of impotence, the really preferred drugs are those which produce vasodilation by direct action on the arteries themselves. Preferably, these include isoxsuprine hydrochloride, nylidrin hydrochloride, tolazoline hydrochloride, and nicotinyl alcohol. Isoxsuprine increases blood flow by direct relaxation of the vascular musculature. The drug also has a slight adrenergic blocking action, but this is not essential to its vasodilating effect. While the drug is known to have value in certain obliterative vascular diseases, such as arteriosclerosis and endarteritis obliterans, and in vasospastic diseases, its use in the manner of the subject invention is novel. The preferred dosage is 3 to 5 milligrams, far less than the normal oral dosage of 10 to 20 milligrams or the normal intramuscular dosage of 5 to 10 milligrams, and therefore very safe.

Nylidrin is a sympathomimetic amine and exerts a pharmacologic action on skeletal muscle blood vessels similar to that of epinephrine. Nylidrin increases blood flow by a direct vasodilating action on the arteries, and has no significant effect on pulse rate or blood pressure. While it does have various known uses, its use as proposed in the method of the subject invention is novel. The 3 to 5 milligram dosage for intramuscular administration of nylidrin is low, thus minimizing the possibility of adverse side effects.

Tolazoline is an adrenergic blocking agent related structurally to both histamine (a vasodilator) and epinephrine. Tolazoline also acts by a direct dilating effect on the walls of blood vessels, and provides a sympathetic block, probably at the terminations of sympathetic nerves. It also has an anti-adrenergic effect which blocks the vasoconstrictive action of epinephrine and levarterenol (Levophed). While tolazoline is also used in the treatment of various peripheral vascular disorders (by oral administration), the use prescribed for the subject invention is novel. The preferred dosage for use in the method of the subject invention is 10 to 25 milligrams, much less than the normal subcutaneous, intramuscular, or intravenous dosage (up to 75 milligrams four times a day), and therefore safe.

Nicotinyl alcohol is converted to nicotinic acid in the body and produces peripheral vasodilation, thereby increasing blood flow to extremities when administered orally. Intramuscular injection results in increased blood flow in the area of injection. The dosage preferred for the method of the subject invention is 10 to 25 milligrams, much less than the normally prescribed oral dosage of 50 to 200 milligrams four times a day. A disadvantage of this drug is that side effects such as flushing of the face and gastrointestinal disturbances may result, particularly at high dosage, although tolerance may develop after prolonged administration. Side effects should generally be minimal with the dosage of the subject method.

In administering the various drugs with the syringe described herein, the injections are made on any area of the dorsal side of the penis where both corpora cavernosa are accessible by injection. The needles of the syringe should be placed equidistant from the subcutaneous dorsal vein (48 in FIG. 5), which is easily visible. The needles are preferably inserted all the way into the corpora cavernosa, thus resulting in an intra-corpora cavernosa injection. The fluid is then secreted into the area of the deeper, profunda arteries 42 in the corpora cavernosa, although essentially the same effect results from subcutaneous injection into the area of the more superficial, dorsal arteries 44. Ideally, the syringe is available pre-loaded for use, which is quite easy as the needles are simply inserted up to the curved stop 18 (as in FIG. 5), and there is almost no pain as the inside diameter of the needles need not be very large, relative to conventional hypodermics, to pass the types of drugs used in the subject method.

Use of the subject invention in alleviating the problems of impotence is far superior to other methods since it is totally unobtrusive and is something of which the female sex partner is totally unaware. Since this method of treatment provides vasodilation without treatment of the nervous aspect of inducing an erection, erection may be sustained for a substantial period of time — up to 2 or 3 hours. In contrast, treatments involving devices to produce local stimulation, thereby inducing an erection, will sustain the erection for only a short period since the nervous fibers are fatigued after a short time. Beyond this time the stimulus no longer elicits a satisfactory response, thus rendering the impotent male who suffers from a significant degree of psychologically oriented impotence even less confident than he was before the treatment.

The subject invention can be a confidence builder to the male, since certain types of impotence that are psychogenically related may be totally overcome by several successful attempts, eliminating future need for the injections. Using the subject invention as an aid convinces the male that he is not totally or absolutely impotent, and in some cases, restores natural, unaided ability to have and sustain an erection for a period long enough to engage in the desired activity. As indicated above, impotence may be defined as the male's inability to develop or sustain an erection of the penis sufficient to conclude coitus or orgasm and ejaculation to his own satisfaction. Although the subject invention is intended to produce or enhance an erection, and not to increase the user's potential for ejaculation (and certainly not to have any effect on fertility), the invention may have a beneficial effect on problems such as the failure to ejaculate. This is because of the confidence building effect that results from repeated successes using the invention, probably preceded by repeated failures using other impotence treatments. This secondary objective is accomplished without directly treating the psychogenic or nervous aspect of impotence, an aspect that is present at least to a certain degree in many impotence cases.

In view of the preceding description of several embodiments of the invention, including the dual needle syringe, alternative embodiments may be apparent to those skilled in the art. Accordingly, the embodiments described and illustrated herein are to be construed as merely illustrative of the application of the principles of this invention, and for the purpose of teaching and enabling those skilled in the art to make and use the invention. The preferred embodiment of the invention described and shown herein is to be understood to be the best mode presently contemplated, but is by no means the only embodiment possible. Numerous other arrangements and modifications may be made in the method and in the syringe using this method without departing from the scope of this invention as defined in the following claims and all equivalents thereto. For example, the erectile tissues of the penis may be injected individually and/or subcutaneously, and the treatment may even be on the surface. Further, vasodilators not discussed herein may be used in practicing the subject invention method of treating impotence. Accordingly, the scope of the invention is defined by the claims and all their equivalents falling within the true spirit and scope of the invention.

What is claimed is:

1. A method of effecting and enhancing an erection of the penis by injecting into the penis a predetermined amount of an appropriate vasodilator.

2. The method of claim 1, wherein multiple injections into the penis are made simultaneously.

3. The method of claim 1, wherein the injection is into the corpora cavernosa.

4. The method of claim 1, wherein the injection is into the corpus spongiosum.

5. The method of claim 1, wherein the injection is subcutaneous, into the area of the dorsal arteries.

6. The method of claim 1, wherein said vasodilator is a sympathomimetic amine.

7. The method of claim 6, wherein said sympathomimetic amine is nylidrin hydrochloride.

8. The method of claim 1, wherein said vasodilator is an adrenergic blocking agent.

9. The method of claim 8, wherein said adrenergic blocking agent is tolazoline hydrochloride.

10. The method of claim 1, wherein said vasodilator is isoxsuprine hydrochloride.

11. The method of claim 1, wherein said vasodilator is nicotinyl alchohol.

* * * * *

REEXAMINATION CERTIFICATE (2751th)

United States Patent [19]
Latorre

[11] B1 4,127,118
[45] Certificate Issued Dec. 19, 1995

[54] METHOD OF EFFECTING AND ENHANCING AN ERECTION

[76] Inventor: Alvaro Latorre, 721 Cervantes, El Paso, Tex. 79922

Reexamination Request:
No. 90/003,587, Sep. 19, 1994

Reexamination Certificate for:
Patent No.: 4,127,118
Issued: Nov. 28, 1978
Appl. No.: 778,047
Filed: Mar. 16, 1977

[51] Int. Cl.$^6$ ............................................. A61F 5/41
[52] U.S. Cl. ............................................. 600/38
[58] Field of Search ............................................. 600/38

[56] References Cited

U.S. PATENT DOCUMENTS 3,552,394  1/1971  Horn .
3,919,425  11/1975  Vidrio .

OTHER PUBLICATIONS

Henderson et al. "On the Mechanism of Erection" (The American Journal of Physiology, Vo. 102, No. 2, pp. 441–448).

Gittes et al. (Urology, vol. IV, No. 4, Oct., 1974, pp. 473–474).

Guyton (*Textbook of Medical Physiology*, W. B. Saunders Co., 1971, p. 950).

Goodman et al. (*The Pharmacological Basis of Therapeutics*, Macmillan, 1975, pp. 467–475, 477–513, 542–547, 736–737).

*Primary Examiner*—Lee S. Cohen

[57] ABSTRACT

A method of alleviating and treating male impotence by effecting and enhancing an erection by injecting into the penis an appropriate vasodilator, a sympathomimetic amine, or an adrenergic blocking agent.

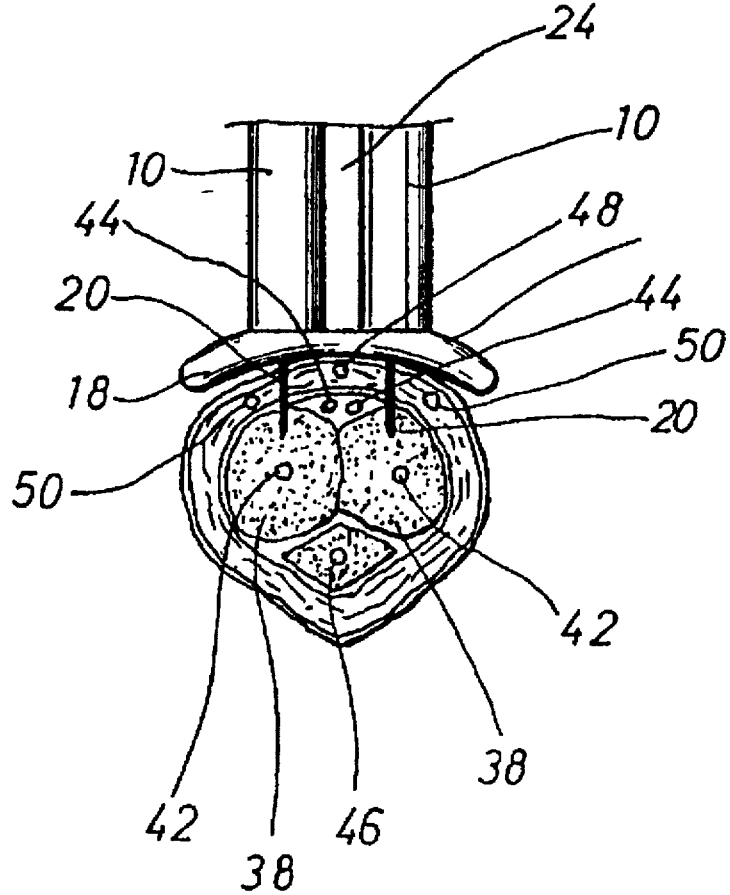

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-11 is confirmed.

* * * * *